US008765238B2

(12) United States Patent
Atanasoska et al.

(10) Patent No.: US 8,765,238 B2
(45) Date of Patent: Jul. 1, 2014

(54) POLYMERIC/INORGANIC COMPOSITE MATERIALS FOR USE IN MEDICAL DEVICES

(75) Inventors: Liliana Atanasoska, Edina, MN (US); Jan Weber, Maastricht (NL); Robert Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1172 days.

(21) Appl. No.: 12/406,212

(22) Filed: Mar. 18, 2009

(65) Prior Publication Data

US 2010/0241071 A1    Sep. 23, 2010

(51) Int. Cl.
| | |
|---|---|
| B32B 1/00 | (2006.01) |
| A61K 9/00 | (2006.01) |
| A61M 29/00 | (2006.01) |
| A61M 31/00 | (2006.01) |
| A61L 29/08 | (2006.01) |
| A61L 27/54 | (2006.01) |
| A61L 27/34 | (2006.01) |
| A61L 29/16 | (2006.01) |

(52) U.S. Cl.
CPC .............. *A61L 27/34* (2013.01); *A61L 29/085* (2013.01); *A61L 27/54* (2013.01); *A61L 29/16* (2013.01); *A61L 2300/608* (2013.01); *A61L 2420/04* (2013.01)
USPC ....... 428/34.7; 428/35.2; 428/35.4; 428/35.8; 428/36.4; 428/36.8; 428/36.91; 424/422; 424/423; 604/96.01; 604/103.06; 604/103.12

(58) Field of Classification Search
CPC . A61M 25/10; A61M 25/104; A61M 31/002; A61M 2025/105; A61M 2025/1075; A61L 27/30; A61L 27/306; A61L 27/34; A61L 27/54; A61L 29/02; A61L 29/10; A61L 29/106; A61L 2300/608; A61L 2420/04; A61K 9/0024; A61K 2300/00; B32B 1/00; B32B 1/02; B32B 7/04; B32B 18/00
USPC ........... 428/34.1, 34.4, 34.6, 34.7, 35.2–35.4, 428/35.7–36.2, 36.4, 36.6, 36.7, 36.8, 36.9, 428/36.91; 424/422–425; 604/96.01, 604/103.02, 103.06, 103.12
See application file for complete search history.

(56) References Cited

U.S. PATENT DOCUMENTS

| | | | |
|---|---|---|---|
| 6,545,097 B2 | 4/2003 | Pinchuk et al. | |
| 7,914,806 B2 * | 3/2011 | Strickler et al. | 424/422 |
| 2005/0038498 A1 | 2/2005 | Dubrow et al. | |
| 2006/0235127 A1 * | 10/2006 | Moad et al. | 524/444 |
| 2007/0104860 A1 | 5/2007 | Gleason et al. | |
| 2007/0299518 A1 | 12/2007 | Ruane | |

FOREIGN PATENT DOCUMENTS

WO    2004005533    1/2004

OTHER PUBLICATIONS

"Acid hydrogen" entry at dictionary.reference.com (accessed Sep. 22, 2012) (http://dictionary.reference.com/browse/acid+hydrogen), 3 pages.*
G.K. Toworfe et al., "Nucleation and growth of calcium phosphate on amine-, carboxyl-, and hydroxyl-silane self assembled monolayers," Biomaterials 27 (2006) 631-642.
T. Yoshioka et al., "Preparation of Alginic Acid Layers on Stainless-steel Substrates for Biomedical Applications," Biomaterials 24 (2003) 2889-2894.
W.G. Pitt et al., "Attachment of hyaluronan to metallic surfaces," J. Biomed. Mater. Res. 68A (2004) 95-106.
H. Zhao et al., "Fabrication of a molecular-level multilayer film on organic polymer surfaces via chemical bonding assembly," Langmuir 23 (2007) 1810-1814.
R. J. Kleisner et al., "A system based on metal alkyl species that forms chemically bound organic overlayers on hydroxylated planar surfaces," Thin Solid Films 381 (2001) 10-14.
I. Kirisci et al., "Tubular inorganic nanostructures," Current Applied Physics 6 (2006) 212-215.
J. Yu et al., "Enhanced photoinduced super-hydrophilicity of the sol-gel-derived TiO2 thin films by Fe-doping," Materials Chemistry and Physics, 95 (2006) 193-196.
Yang et al., "Composite thin film by hydrogen-bonding assembly of polymer brush and poly(vinylpyrrolidone)," Langmuir 22 (2006) 338-343.
Pyun and Matyjaszewski, "Synthesis of Nanocomposite Organic/Inorganic Hybrid Materials Using Controlled "Living" Radical Polymerization," Chem. Mater., 13 (2001) 3436-3448.
B. Reeves, "Recent Advances in Living Free Radical Polymerization," Nov. 20, 2001, University of Florida.
T. Kowalewski et al., "Complex nanostructured materials from segmented copolymers prepared by ATRP," Eur. Phys. J.E., 10 (2003) 5-16.
R. Boukherroub, "Chemical reactivity of hydrogen-terminated crystalline silicon surfaces," Current Opinion in Solid State and Materials Science 9 (2005) 66-72.
G.K. Jennings et al., "Physicochemical Properties of Surface-Initiated Polymer Films in the Modification and Processing of Materials," Adv. Mater., 16(22) (2004) 1983-1994.
C.D. Vo et al., "Surface ATRP of hydrophilic monomers from ultrafine aqueous silica sols using anionic polyelectrolytic macroinitiators," Langmuir, 23 (2007) 408-413.
C. Perruchot et al., "XPS characterisation of core-shell silica-polymer composite particles synthesised by atom transfer radical polymerisation in aqueous media," European Polymer Journal 40 (2004) 2129-2141.
W. Senaratne et al., "Self-Assembled Monolayers and Polymer Brushes in Biotechnology: Current Applications and Future Perspectives," Biomacromolecules, 6 (2005) 2427-2448.
Viitala R. et al., "Surface properties of in vitro bioactive and non-bioactive sol-gel derived materials," Biomaterials, Aug. 2002, 23(15), 3073-3086.

(Continued)

*Primary Examiner* — Walter B Aughenbaugh
(74) *Attorney, Agent, or Firm* — Vidas, Arrett & Steinkraus

(57) ABSTRACT

In one aspect, the present invention provides composite coatings for implantable or insertable medical devices. These composite coatings comprise (a) an inorganic portion and (b) a polymeric portion that comprises a poly(vinyl pyrrolidone) (PVP) block.

10 Claims, No Drawings

(56) References Cited

OTHER PUBLICATIONS

G. Kickelbick, "Concepts for the incorporation of inorganic building blocks into organic polymers on a nanoscale," Prog. Polym. Sci., 28 (2003) 83-114.

C.-K. Chan et al., "Interfacial interactions and their influence to phase behavior in poly(vinyl pyrrolidone)/silica hybrid materials prepared by sol-gel process," Materials Letters 58 (2004) 2243-2247.

M. Yoshida et al., "Sol-Gel-Processed $SiO_2/TiO_2$/Poly(vinylpyrrolidone) Composite Materials for Optical Waveguides," Chem. Mater., 8(1) (1996) 235-241.

M. Zheng et al., "Preparation, structure and properties of $TiO_2$-PVP hybrid films," Mater. Sci. Eng., B, Solid-State Mater. Adv. Technol. 77(1) (2000) 55-59.

J. Shen et al., "Preparation of zirconia thin films via sol-gel process from inorganic precursor," Proc. SPIE vol. 4086, p. 406-409, 2000, Fourth International Conference on Thin Film Physics and Applications.

M-P Zheng et al., "Characterization of $TiO_2$-PVP nanocomposites prepared by the sol-gel method," Journal of Materials Science Letters, 19(5) 2000 433-436.

K. Takana et al., "Sol-Gel Preparation and Mechanical Properties of Machinable Cellulose/Silica and Polyvinylpyrrolidone/Silica Composites," Chemistry and Material Science 32(1-3) 2004 pp. 73-77.

K. Chan et al., "Initiated chemical vapor deposition of polyvinylpyrrolidone-based thin films," Polymer 47 (2006) 6941-6947.

Martin et al., "Initiated chemical vapor deposition of antimicrobial polymer coatings," Biomaterials 28 (2007) 909-915.

Zhao et al., "Designing Nanostructures by Glancing Angle Deposition," Proceedings of SPIE vol. 5219, 59-73, 2003.

R.A. Zoppi et al., "Hybrids of Poly(ethylene oxide-b-amide-6) and $ZrO_2$ Sol-gel: Preparation, Characterization, and Application in Processes of Membranes Separation," Advances in Polymer Technology, 21(1), 2006, 2-16.

R.A. Zoppi et al., "Hybrid films of poly(ethylene oxide-b-amide-6) containing sol-gel silicon or titanium oxide as inorganic fillers: effect of morphology and mechanical properties on gas permeability," Polymer 41 (2000) 5461-5470.

M.L. Sforca et al., "Hybrid Membranes Based on $SiO_2$/Polyether-b-Polyamide: Morphology and Applications," Journal of Applied Polymer Science, 82(1), 2001, 178-185.

* cited by examiner

US 8,765,238 B2

POLYMERIC/INORGANIC COMPOSITE MATERIALS FOR USE IN MEDICAL DEVICES

FIELD OF THE INVENTION

The present invention relates to medical devices and more particularly to medical devices containing polymeric/inorganic composite materials.

BACKGROUND OF THE INVENTION

Various medical devices are known which are configured for implantation or insertion into a subject. Coatings for such devices have various attendant property requirements, including physical and chemical property requirements, which can be quite demanding.

SUMMARY OF THE INVENTION

According to one aspect, the present invention provides composite coatings for implantable or insertable medical devices. These composite coatings comprise (a) an inorganic portion and (b) a polymeric portion that comprises a poly(vinyl pyrrolidone) (PVP) block.

Advantages of the present invention include one or more of the following, among others: (a) medical devices may be supplied with polymeric/inorganic composite coatings that provide for enhanced mechanical characteristics, for example, enhanced strength, toughness and/or abrasion resistance; (b) medical devices may be supplied with polymeric/inorganic composite coatings that provide enhanced adhesion to underlying substrate materials; and (c) medical devices may be supplied with polymeric/inorganic composite coatings that provide for enhanced biocompatibility.

These and other aspects, embodiments and advantages of the present invention will become immediately apparent to those of ordinary skill in the art upon review of the Detailed Description and Claims to follow.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety In one aspect, the present invention provides composite coatings for implantable or insertable medical devices. These composite coatings comprise (a) an inorganic portion and (b) a polymeric portion that comprises a poly(vinyl pyrrolidone) (PVP) block.

As used herein, a "composite" coating is one that is both inorganic and organic (e.g., polymeric) in composition.

As used herein, "polymers" are molecules that contain multiple copies (e.g., 5 to 10 to 25 to 50 to 100 to 250 to 500 to 1000 or more copies) of one or more constitutional units, commonly referred to as monomers. As used herein, "monomers" may refer to free monomers and those that are incorporated into polymers, with the distinction being clear from the context in which the term is used.

Polymers may take on a number of configurations, which may be selected, for example, from linear, cyclic, and branched configurations. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), network configurations (e.g., crosslinked polymers), and so forth.

As used herein, "homopolymers" are polymers that contain multiple copies of a single constitutional unit (i.e., monomer). "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more differing polymer blocks, for instance, because a constitutional unit is found in one polymer block that is not found in another polymer block.

As used herein, a "polymer block" is a grouping of constitutional units (e.g., 5 to 10 to 25 to 50 to 100 to 250 to 500 to 1000 or more units) and thus may correspond to an entire polymer molecule or may be a part of a larger entity (e.g., a block copolymer, a polymer brush, etc.). Blocks can be branched or unbranched. Blocks can contain a single type of constitutional unit (also referred to herein as "homopolymer blocks") or multiple types of constitutional units (also referred to herein as "copolymer blocks") which may be provided, for example, in a random, statistical, gradient, or periodic (e.g., alternating) distribution. As used herein, a "chain" is a linear (unbranched) grouping of constitutional units (i.e., a linear block).

Specific medical devices which may employ composite coatings in accordance with the present invention include a wide variety of implantable or insertable medical devices. Examples include balloons, catheters (e.g., renal or vascular catheters such as balloon catheters), guide wires, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils) and embolic particles, myocardial plugs, pacemaker leads, neural stimulation devices, left ventricular assist hearts and pumps, total artificial hearts, heart valves, vascular valves, tissue bulking devices, sutures, suture anchors, anastomosis clips and rings, cochlear implants, tissue staples and ligating clips at surgical sites, cannulae, metal wire ligatures, orthopedic prosthesis such as bone grafts, bone plates, fins and fusion devices, joint prostheses, implantable identification devices including subcutaneous implantable RF identification tags, as well as various other medical devices that are adapted for implantation or insertion into the body.

The medical devices of the present invention include implantable and insertable medical devices that are used for diagnosis, for identification, for systemic treatment, or for the localized treatment of any tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, nervous system, liver and pancreas, skeletal muscle, smooth muscle, breast, dermal tissue, cartilage, tooth and bone. As used herein, "treatment" refers to the prevention of a disease or condition, the reduction or elimination of symptoms associated with a disease or condition, or the substantial or complete elimination of a disease or condition. Typical subjects (also referred to as "patients") are vertebrate subjects, more typically mammalian subjects, and include humans, pets and livestock.

In some embodiments, the composite coatings cover an entire medical device or medical device component. In some embodiments, the composite coatings cover only a portion of a medical device or medical device component. The composite coatings can be provided over underlying substrates in a variety of shapes (e.g., in desired patterns) and in a variety of locations. Multiple composite coatings may be provided, for example, laterally relative to one another or stacked upon one another. Where multiple composite coatings are provided, they may be formed from a variety of composite materials (e.g., composite layers having different compositions may be provided at different locations over an underlying substrate).

In some embodiments of the invention, therapeutic agents are disposed within or beneath the composite coatings.

Materials for use as underlying substrate materials for the composite coatings of the invention include organic materials including polymeric materials and inorganic materials including metallic materials, ceramic materials, and further non-metallic inorganic materials such as carbon-based and silicon-based materials, as well as combinations of the forgoing, among others.

Specific examples of non-metallic inorganic materials may be selected, for example, from materials containing one or more of the following: metal oxides, including aluminum oxides and transition metal oxides (e.g., oxides of titanium, zirconium, hafnium, ruthenium, tantalum, molybdenum, tungsten, rhenium, iridium, etc.); silicon; silicon-based ceramics, such as those containing silicon nitrides, silicon carbides and silicon oxides (sometimes referred to as glass ceramics); calcium phosphate ceramics (e.g., hydroxyapatite); carbon and carbon-based, ceramic-like materials such as carbon nitrides, among others.

Specific examples of metallic inorganic materials may be selected, for example, from materials containing one or more of the following: metals (e.g., gold, platinum, palladium, iridium, osmium, rhodium, titanium, tantalum, tungsten, and ruthenium) and metal alloys, including metal alloys comprising iron and chromium (e.g., stainless steels, including platinum-enriched radiopaque stainless steel), niobium alloys, titanium alloys including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys), among others.

Specific examples of polymeric substrate materials may be selected, for example, from materials containing one or more of the following polymers: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones; polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®; p-xylylene polymers; polyiminocarbonates; copoly (ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as further copolymers of the above.

Certain metals, ceramics and polymers have surface hydroxyl groups which may, for example, hydrogen bond with the PVP in the composite coatings in some embodiments of the invention, thereby enhancing adhesion between the substrate and an adjacent composite coating. The hydrogen bonding abilities of PVP are discussed below.

In certain embodiments of the invention, a substrate is formed using a block copolymer that comprises a low Tg block and a high Tg block. As used herein, a "low Tg polymer block" is one that displays a Tg that is below normal body temperature, more typically from 35° C. to 20° C. to 0° C. to −25° C. to −50° C. or below. Conversely, as used herein, an elevated or "high Tg polymer block" is one that displays a Tg that is above normal body temperature, more typically from 40° C. to 50° C. to 75° C. to 100° C. or above. Tg can be measured by differential scanning calorimetry (DSC). In general, low Tg polymer blocks are soft and elastomeric at body temperature, whereas high Tg polymer blocks are hard.

In certain embodiments, the substrate may be formed using a block copolymer that comprises a low Tg block and two high Tg blocks, wherein at least a portion of the low Tg block separates the high Tg blocks (in other words, block copolymers in which high Tg blocks are interconnected via a low Tg block). Examples of this architecture include, for example, the following configurations (in which low Tg polymer chains are designated "L" and high Tg polymer chains are designated "H") among many others: (a) block copolymers having alternating chains of the type HLH, (LH)m, L(HL)m and H(LH)m where m is a positive whole number of 2 or more, (b) multiarm (including star) copolymers such as X(LH)m, where X is a hub species (e.g., an initiator molecule residue, a linking residue, etc.), and (c) comb copolymers having an L chain backbone and multiple H side chains.

Block copolymers like those described above tend to phase separate into hard phase domains and elastomeric phase domains. Polymers of this type are capable of demonstrating high strength and elastomeric properties, while at the same time being processable using techniques such as solvent- and/or melt-based processing techniques. Without wishing to be bound by theory, it is believed that the hard phase domains act as physical crosslinks for the material. Moreover, because the crosslinks are not covalent in nature, they can be reversed, for example, by dissolving or melting the block copolymer.

Some specific examples of low Tg polymer blocks include the following, among others: (a) low Tg polyacrylate blocks including homopolymer and copolymer blocks containing ethyl acrylate, butyl acrylate and/or other alkyl acrylate monomers, (b) low Tg polyalkene blocks including homopolymer and copolymer blocks containing ethylene, propylene, isobutylene, butadiene and/or other alkene monomers (c) low Tg polysiloxane blocks including homopolymer and copolymer blocks containing dimethylsiloxane, diethylsiloxane, methylethylsiloxane and/or other siloxane monomers, (d) low Tg polyether blocks including homopolymer and copolymer blocks containing methyl vinyl ether, ethylene oxide, trimethylene oxide, propylene oxide, tetramethylene oxide, other vinyl ethers, other cyclic ethers, and combinations thereof, and (e) poly(alkyl vinyl ether) blocks including homopolymer and copolymer blocks containing methyl vinyl ether, ethyl vinyl ether and/or other alkyl vinyl ethers.

Some specific examples of high Tg blocks include the following, among others: (a) high Tg polyvinyl aromatic blocks including homopolymer and copolymer blocks containing styrene, alpha-methyl styrene, sulfonated styrene, and/or other styrene derivatives, (b) high Tg polyamide blocks selected from nylon homopolymer and copolymer blocks such as nylon 6, nylon 4/6, nylon 6/6, nylon 6/10, nylon 6/12, nylon 11 and nylon 12 blocks, (c) high Tg polymethacrylate blocks including homopolymer and copolymer blocks containing methyl methacrylate, t-butyl methacrylate, hydroxyethyl methacrylate and/or other methacrylate monomers, (d) high Tg polyvinyl ether blocks including homopolymer and copolymer blocks containing cyclohexyl vinyl ether and/or other vinyl ether monomers, (e) high Tg poly(hydroxyalkyl methacrylates) blocks including homopolymer and copolymer blocks containing 2-hydroxyethyl methacrylate, 2-hydroxypropyl methacrylate, and/or other hydroxyalkyl methacrylates.

Specific examples of block copolymers include poly(tetramethylene oxide)-nylon-12 block copolymers, specifically segmented block copolymers with alternating nylon-12 hard blocks and polytetramethylene oxide soft blocks, available from Elf Atochem as PEBAX, poly(styrene-b-ethylene/butylene-b-styrene) (SEBS) triblock copolymers, available from Kraton Polymers LLC as Kraton® G series polymers, and poly(styrene-b-isobutylene-b-styrene) triblock copolymers (SIBS), disclosed in U.S. Pat. No. 6,545,097 to Pinchuk, incorporated by reference herein, among many others.

In certain embodiments of the invention, a composite coating is provided which contains a polymer block that has the same monomer composition as a polymer block within an underlying polymeric substrate, thereby enhancing adhesion between the composite coating and the substrate. For example, where the substrate comprises a block copolymer that comprises first and second polymer blocks of differing monomer composition, the composite coating may comprise a polymer block having the same monomer composition as the first polymer block, a polymer block having the same monomer composition as the second polymer block, or both. Various ways by which polymer blocks may be incorporated into composite coatings are described below.

In certain embodiments, adhesion between a composite coating and substrate is enhanced by derivatizing the substrate with organic functional groups such as epoxy, carboxyl, amino, hydroxyl, or isocyanate groups, among others. For example, G. K. Toworfe et al., *Biomaterials* 27 (2006) 631-642 describe the creation of amine (e.g., —NH$_2$), carboxyl (—COOH) and hydroxyl (—OH) functionalized surfaces by grafting amine, carboxyl and hydroxyl functionalized alkoxysilanes (i.e., 3-aminopropyltriethoxysilane, 3-triethoxysilylpropyl succinic anhydride and glycidoxypropyl tri-methoxysilane, respectively), onto oxidized silicon wafers. Functionalization techniques would also be suitable for other inorganic substrates, such as metallic (e.g., stainless steel, titanium, etc.), metal oxide and nitride substrates, or organic substrates, such as polymeric substrates, including essentially any substrate is or can be functionalized with organic functional groups such as the preceding, among others. See, e.g., T. Yoshioka et al. Biomaterials 24 (2003) 2889-2894 (describing aminopropyltriethoxysilane-grafted stainless-steel), W. G. Pitt et al., *J. Biomed. Mater. Res.* 68A (2004) 95-106 (describing surface modification of stainless steel by covalent attachment of an epoxy silane), H. Zhao et al., *Langmuir* 23 (2007) 1810-1814 (describing formation of hydroxylated polymers such as hydroxylated polypropylene via a sulfonated intermediate), and R. J. Kleisner et al., *Thin Solid Films* 381 (2001) 10-14 (describing chemically bound organic layers formed from dimethyl-zinc and alkane-thiols on hydroxylated oxide surfaces, oxidized silicon and glass), each of which is incorporated by reference herein.

As indicated above, the composite coatings of the present invention comprise (a) an inorganic portion and (b) a polymeric portion comprising a poly(vinyl pyrrolidone) block.

The polymeric and inorganic portions in the coating may be associated with one another via covalent bonding and/or non-covalent interactions, for example, electrostatic interactions such as charge-charge interactions, charge-dipole interactions, and dipole-dipole interactions (including hydrogen bonding).

The distribution of the polymeric and inorganic portions within the composite coatings may vary widely, depending on many factors including the technique used to construct the composite coatings. For example, the distribution may vary from a continuous polymeric portion with an inorganic portion incorporated at the molecular level, to a continuous polymeric portion with a dispersed particulate inorganic portion, to a bi-continuous system, to a continuous inorganic portion with a dispersed particulate polymeric portion, to a continuous inorganic portion with a polymeric portion incorporated at the molecular level, to a bi-disperse system (e.g., alternating polymeric and inorganic layers), among various other possibilities. Moreover, the polymeric portion of the composite coating may have multiple polymeric phases, and the inorganic portion of the composite coating may have multiple inorganic phases. For example, multiple polymeric phases will typically exist where the polymeric portion comprises a block copolymer or a blend of different polymers, whereas multiple inorganic phases will exist where two types of inorganic particles are present within the composite coating, among numerous other possibilities. For improved material properties, at least one of the polymeric and inorganic portions may correspond to phases of nanoscale dimension by which is meant that at least one cross-sectional dimension of the phases (e.g., the diameter for spherical or cylindrical phases, the thickness for ribbon-shaped, plate-shaped or layered phases, etc.) is less than 1 micron (1000 nm), for example, ranging from 1000 nm to 300 nm to 100 nm to 30 nm to 10 nm or less in some embodiments. A decrease in such dimensions generally results in an increase in the interfacial area that exists between the various phases.

The inorganic portions of the composite coatings of the invention can be formed from metallic inorganic materials, non-metallic inorganic materials, and combinations thereof. Suitable inorganic materials can be selected from those set forth above in connection with substrate materials, among others. The inorganic portion may vary from 1 wt % or less to 2 wt % to 5 wt % to 10 wt % to 25 wt % to 50 wt % to 75 wt % to 90 wt % to 95 wt % to 98 wt % to 99 wt % or more of the composite coating.

In some embodiments, the inorganic portion includes inorganic particles. Examples of suitable particles for this purpose include nanoparticles, which are particles having at least one dimension (e.g., the thickness) that is less than 1000 nm (e.g., at least the diameter for a nanofiber or nanotube, the thickness for a nanoplate or nanoribbon, the diameter for a nanosphere, etc.), for example, having at least one dimension ranging from 1000 nm to 300 nm to 100 nm to 30 nm to 10 nm or less.

Inorganic particles suitable for use in the composite coatings of the invention thus include plates, tubes, fibers, spheres, and other regular and irregular particle shapes. Specific examples of plates include synthetic or natural phyllosilicates including clays and micas (which may optionally be intercalated and/or exfoliated) such as montmorillonite, hectorite, hydrotalcite, vermiculite and laponite. Specific examples of tubes and fibers include single-wall and multi-wall (including so-called "few-wall") carbon nanotubes, silica and titania nanotubes (see, e.g., I. Kirisci et al., "Tubular inorganic nanostructures," *Current Applied Physics* 6 (2006) 212-215), incorporated by reference herein, vapor grown carbon fibers, alumina fibers, titanium oxide fibers, tungsten oxide fibers, tantalum oxide fibers, zirconium oxide fibers, and silicate fibers such as aluminum silicate fibers. Further specific examples include regular and irregular particles such as fullerenes (e.g., "Buckey balls"), silica particles, aluminum oxide particles, titanium oxide particles, tungsten oxide particles, tantalum oxide particles, zirconium oxide particles, sol-gel derived metal and semi-metal oxide particles, polyhedral oligomeric silsequioxanes (POSS) including various functionalized POSS and polymerized POSS, and polyoxometalates (POMs).

The inorganic portion of the composite coating can have a major effect upon the properties of the composite coating. For instance, the robustness of the coating may be enhanced by the inclusion of an inorganic portion (e.g., particles such as POSS, carbon nanotubes, etc. or sol-gel derived oxides such as silica, titania, etc.). In some embodiments, the composite coating is may be rendered more radiopaque by adding heavy metal inorganics (e.g., barium oxides, etc.). In some embodiments, the composite coating may be rendered hydrophilic or hydrophobic. For example, $TiO_2$ doped with $Fe^{3+}$ is known to show photo-induced super-hydrophilicity. See J. Yu et al., *Materials Chemistry and Physics*, 95 (2006) 193-196, incorporated by reference herein. This technique may also be employed wherein a photo-induced hydrophobic inner surface and a super-hydrophilic outer surface is desirable.

Hydrophobic effects may be useful in dry environments. For instance, it may be desirable to provide a lubricious hydrophobic inner tubular member for a balloon catheter to allow for ease of movement over a guide wire. Hydrophobic effects may also be useful, for instance, in maintaining a hydrophobic drug on medical device surface within an aqueous environment. For example, one may provide a guide wire with dots of a hydrophobic material (e.g., on the convex surface of the guide wire or within small depressions, or dimples, on the guide wire surface). Upon exposure to a drug (e.g., dipping the guide wire into drug dissolved in a hydrophobic solvent), the drug will preferentially associate with the dots of hydrophobic material, particularly where the remainder of the wire is hydrophilic. Hydrophobic effects may also be used to reduce or prevent in vivo crystallization from occurring on the surface of various devices, for example, urethral, ureteral and biliary stents. See, e.g., Pub. No. US 2005/0038498, incorporated by reference herein.

Depending on the nature of the underlying substrate, adhesion to the substrate may be enhanced in some embodiments by employing coatings with an organo-functionalized inorganic portion, for example, epoxy, hydroxyl, carboxyl, amino, or isocyanate functionality, among others.

As noted above, the polymeric portions of the composite coatings of the invention comprise PVP blocks. PVP is desirable for use in medical device coatings due to a unique combination of properties, such as solubility in water and a range of organic solvents, non-toxicity, complexing ability vis-à-vis various organic and inorganic compounds, good film forming ability and biocompatibility (e.g., PVP has been used in the biomedical field, for instance, as a blood plasma expander; moreover, as a polymeric carrier, PVP has been shown to prolong the plasma circulation lifetime of bioconjugated drugs). In addition to PVP blocks, the polymeric portions may contain additional polymer blocks other than PVP. The PVP and optional additional polymer blocks may be provided within a single polymeric entity (e.g., as blocks within a block copolymer) or as distinct polymeric entities. The PVP and/or optional additional polymer blocks may be covalently or non-covalently bound to materials making up the inorganic portion of the composite coating.

Optional additional polymer blocks may be selected, for example, from the various polymers set forth above in connection with substrate materials, among others.

Examples of optional additional polymer blocks further include hydrophilic polymer blocks for example, polyionic blocks, including polycationic blocks and polyanionic blocks, and other hydrophilic blocks. Specific examples of polycationic blocks may be selected, for example, from suitable members of the following and their salts (e.g., HCl salts): polyamines, including polyamidoamines, poly(amino methacrylates) including poly(dialkylaminoalkyl methacrylates) such as poly(dimethylaminoethyl methacrylate) and poly(diethylaminoethyl methacrylate), polyvinylamines, poly(vinylbenzyltrimethylamines), polyallylamines and poly(diallyldialklylamines) such as poly(diallyldimethylammonium chloride), polyimines including polyalkyleneimines such as polyethyleneimines, polypropyleneimines and ethoxylated polyethyleneimines, polycationic peptides and proteins such as homopolymer and copolymer blocks containing lysine, arginine, ornithine and combinations thereof, among others. Specific examples of polyanionic polymer blocks may be selected, for example, from suitable members of the following and their salts (e.g., ammonium, potassium, sodium, etc., salts): polysulfonates such as polyvinylsulfonates, poly(styrenesulfonates), and sulfonated poly(tetrafluoroethylene), polycarboxylates such as acrylic acid and methacrylic acid polymer blocks, polyanionic peptides and proteins such as polymer and copolymer blocks containing glutamic acid, aspartic acid and combinations thereof, polyphosphates such as phosphoric acid derivatives of various polymer blocks, polyphosphonates such as polyvinylphosphonate blocks, and polysulfates such as polyvinylsulfates, among others. Specific examples of other hydrophilic blocks include homopolymer and copolymer blocks containing one or more of the following monomers: alkylene oxides such as ethylene oxide, hydroxyalkyl methacrylates such as hydroxyethyl methacrylate, and alkyl vinyl ethers such as methyl vinyl ether, among others.

The polymeric portion, including PVP and optional additional polymer blocks, may vary from 1 wt % or less to 2 wt % to 5 wt % to 10 wt % to 25 wt % to 50 wt % to 75 wt % to 90 wt % to 95 wt % to 98 wt % to 99 wt % or more of the composite coating.

As noted above, in some embodiments, an additional polymer block may be included in a composite coating that has the same monomer composition as a polymer block within an underlying polymeric substrate. For instance, such a polymer block may be included to enhance adhesion to the substrate. As a specific example, where the substrate comprises PEBAX, polyether blocks such as poly(tetramethylene oxide), polyamide blocks such as nylon-12, or a combination of both, may be introduced into the composite coating as additional polymer blocks.

Due to the electronegative atoms found therein, PVP can participate in hydrogen bonding with other molecules in which hydrogen is covalently attached to an electronegative group, for instance, a molecule containing N—H or O—H groups. (In a typical hydrogen bonding interaction, a hydrogen atom on one molecule that is attached to O or N is attracted to an O or N of a different molecule.) As a result, composite coatings containing PVP may have enhanced adhesion to underlying substrates having N—H or O—H groups, for example, substrates having polyamine-containing surfaces, polyalcohol-containing surfaces, hydroxylated polymeric surfaces (see, e.g., H. Zhao et al., *Langmuir* 2007, 23, 1810-1814, incorporated by reference herein), silica and glass surfaces, and various metal and metal oxide surfaces, among others.

In some embodiments, at least one additional polymer block is included in composite coatings in accordance with the invention, which additional polymer block comprises hydrogen atoms that are capable of hydrogen bonding with the electronegative atoms found within the PVP (referred to here as "proton donating block"). By providing a coating whose polymeric portion comprises a proton donating block and a poly(vinyl pyrrolidone) block, hydrogen bonding interactions may be obtained which are very strong, even to the extent of stabilizing the coatings when immersed aqueous solutions, without the need for ionic or covalent crosslinking.

In some embodiments, the poly(vinyl pyrrolidone) block and the proton donating block are provided within a single polymer molecule (i.e., in a block copolymer), which may be bound or unbound to an inorganic particle. In some embodiments, the poly(vinyl pyrrolidone) block and the proton donating block are provided within distinct polymer molecules, which may be unbound or bound to a microparticle. Examples of proton donating blocks include polyacids such as poly(acrylic acid), among others, and polyalcohols such as poly(vinyl alcohol) and poly(4-vinyl phenol), among others. Note that where a polyacid is employed, the pH is typically sufficiently acidic to ensure that the acidic protons remain on the polymer (and thus can participate in hydrogen bonding). For example, in Yang et al., infra, in which poly(acrylic acid) polymer blocks are employed, the pH is 3.

The ability of PVP to participate in hydrogen bonding with other polymer blocks creates opportunities for layer-by-layer assembly of composite coatings based on hydrogen bonding.

By way of background, Yang et al., *Langmuir* 22 (2006) 338-343, incorporated by reference herein, describe hydrogen-bonding-based, layer-by-layer assembly of alternating layers of (a) PVP and (b) a spherical polymer brush which contains a poly(methylsilsesquioxane) core and poly(acrylic acid) polymer blocks (so-called "brush hairs") radiating from the cores. The carboxyl groups of the poly(acrylic acid) were reported to provide the hydrogen atoms needed to engage in hydrogen bonding with the PVP for successful layer-by-layer assembly. The initial layer was a PVP layer, which hydrogen bonded with hydroxyl groups on the substrate surface (silicon or quartz). The overall coating thickness was found to be a linear function of the number of bilayers, with the average increase in thickness per bilayer being 28.3 nm. The coatings were further calcined to remove the organic components, yielding a substantailly inorganic film, or treated with tetrabutylammonium fluoride to remove the poly(methylsilsesquioxane) cores, yielding a substantially organic film.

In accordance with an embodiment of the present invention, a medical substrate, which may correspond to a medical device or component thereof, for example, a substrate having N—H or O—H groups (e.g., a substrate having a polyamine, polyalcohol, hydroxylated polymeric, silica, glass, metallic or metal oxide surface) is exposed in an alternating fashion to aqueous solutions of (1) a polymer containing PVP, for example, a polymer containing one or more PVP blocks and, optionally, one or more additional polymer blocks and (2) polymer brushes containing (a) inorganic nanoparticle cores (e.g., formed from inorganic materials such as those set forth above) and (b) covalently or non-covalently attached polymer "brush hairs," for example, containing one or more proton donating blocks, for example, poly(acrylic acid), poly(vinyl alcohol) and/or poly(4-vinyl phenol) and, optionally, one ore more additional polymer blocks. Note that in this embodiment, component "(1)" and component "(2)" each contributes to the polymeric portion of the composite coating, whereas component "(2)" provides the inorganic portion of the composite coating.

In accordance with another embodiment of the present invention, a substrate like that of the prior paragraph may be exposed to alternating aqueous solutions of (1) polymer brushes containing (a) inorganic nanoparticle cores (e.g., formed from inorganic materials such as those set forth above) and (b) covalently or non-covalently attached polymer "brush hairs," for example, containing one or more PVP blocks and, optionally, one or more additional polymer blocks and (2) a polymer containing one or more proton donating blocks and, optionally, one or more additional blocks. In this embodiment, component "(1)" and component "(2)" again contribute to the polymeric portion of the composite coating, whereas component "(1)" provides the inorganic portion of the composite coating.

In other embodiments, a composite coating consisting of a single layer may be formed, for example, a layer containing an inorganic portion and an organic portion including a PVP block and a proton donating block. For example, the coating may contain (a) inorganic particles such as those described above, (b) PVP or a polymer containing one or more PVP blocks and one or more additional polymer blocks, and (c) one or more proton donating polymers, for example, poly (acrylic acid), poly(vinyl alcohol) or poly(4-vinyl phenol) or one or more polymers containing one or more proton donating blocks and one or more additional blocks. As another example, the coating may contain inorganic particles such as those described above and a block copolymer containing one or more PVP blocks and one or more proton donating blocks, such as poly(acrylic acid), poly(vinyl alcohol) and/or poly(4-vinyl phenol) blocks. As another example, the coating may contain a polymer containing PVP, for example, a polymer containing one or more PVP blocks and, optionally, one or more additional polymer blocks, and polymer brushes containing inorganic nanoparticle cores (e.g., formed from inorganic materials such as those set forth above) and covalently or non-covalently attached polymer "brush hairs," for example, containing one or more proton donating blocks and, optionally, one or more additional blocks. As yet another example, the coating may contain a polymer containing one or more proton donating blocks and, optionally, one or more additional polymer blocks, and polymer brushes containing inorganic nanoparticle cores and covalently or non-covalently attached polymer "brush hairs," for example, containing one or more PVP blocks and, optionally, one or more additional blocks.

Various methods are known by which a wide array of polymer blocks may be formed, including cationic, anionic, and radical polymerization methods, particularly controlled/ "living" cationic, anionic and radical polymerizations. Living free radical polymerizations (also called controlled free radical polymerizations) may be employed in various embodiments, due to the undemanding nature of radical polymerizations in combination with the power to control polydispersities, architectures, and molecular eights that living processes provide. Specific examples of controlled free radical polymerization processes include metal-catalyzed atom transfer radical polymerization (ATRP), stable free-radical polymerization (SFRP), including nitroxide-mediated processes (NMP), and degenerative transfer including reversible addition-fragmentation chain transfer (RAFT) processes. Combinations of these techniques may also be employed, for example, in the formation of block copolymers. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), B. Reeves, "Recent Advances in Living Free Radical Polymerization," Nov. 20, 2001. University of Florida, T. Kowalewski et al., "Complex nanostructured materials from segmented copolymers prepared by ATRP," *Eur. Phys. J. E,* 10, 5-16 (2003), each of which is incorporated by reference herein.

Various methods are also known by which a wide array of polymer brushes can be formed including so-called "grafting to" approaches, where a previously formed polymer is attached to a particle surface, and "grafting from" approaches, in which polymers are grown from a particle surface. Sever examples follow, which use ATRP as an exemplary polymerization technique, although other polymerization techniques may be employed as well. As an example of a "grafting from" approach, an ATRP initiator having a thiol or disulfide group can be adsorbed to a particle of gold or another noble metal, followed by polymerization based on ATRP. In another example, an ATRP initiator having an alkoxysilane group can be reacted with hydroxyl groups on a particle surface, followed by polymerization based on ATRP. In another example, an ATRP initiator having a chlorosilane group can be reacted with a silicon oxide particle surface, followed by polymerization based on ATRP. In another example, monolayers covalently grafted onto silicon surfaces with terminal alpha-bromoester, benzyl chloride or aniline moieties may be prepared and used for the immobilization of a wide range of polymer and diblock copolymer brushes via surface initiated ATRP. In another example, a cationic or anionic ATRP initiator is electrostatically bound to a particle of opposite charge, followed by polymerization based on ATRP. For further information, see, e.g., R. Boukherroub, *Current Opinion in Solid State and Materials Science* 9 (2005) 66-72, G. K. Jennings et al., *Adv. Mater.,* 16(22) (2004) 1983-1994, C. D. Vo et al., *Langmuir,* 23 (2007) 408-413, C. Perruchot et al., *European Polymer Journal* 40(2004) 2129-2141, W Senaratne et al., *Biomacromolecules,* 6 (2005) 2427-2448, and references cited therein, each of which is incorporated by reference herein.

In some embodiments, the composite coatings comprise a sol-gel-generated inorganic portion. By way of background, it is well known that inorganic regions may be formed using sol-gel processing. In a typical sol-gel process, precursor materials, typically selected from inorganic metallic and semi-metallic salts, metallic and semi-metallic complexes/ chelates, metallic and semi-metallic hydroxides, and organo-metallic and organo-semi-metallic compounds such as metal alkoxides and alkoxysilanes, are subjected to hydrolysis and condensation (also referred to sometimes as "polymerization") reactions, thereby forming a "sol" (i.e., a suspension of solid particles within a liquid). For example, an alkoxide of choice (such as a methoxide, ethoxide, isopropoxide, tert-butoxide, etc.) of a semi-metal or metal of choice (such as silicon, germanium, aluminum, zirconium, titanium, iron, hafnium, tantalum, molybdenum, tungsten, rhenium, iridium, barium, etc.) may be dissolved in a suitable solvent, for example, in one or more alcohols. Subsequently, water or another aqueous solution such as an acidic or basic aqueous solution (which aqueous solution can further contain organic solvent species such as alcohols) is added, causing hydrolysis and condensation to occur. If desired, additional agents can be added, such as agents to control the viscosity and/or surface tension of the sol, among others. Further processing of the sol enables solid materials to be made in a variety of different forms. For instance, "wet gel" coatings can be produced by dipping, spray coating, coating with an applicator (e.g., by roller or brush), ink-jet printing, screen printing, and so forth. Where dip coating is employed, the rate of withdrawal from the sol can be varied to influence the properties of the gel. The wet gel is then dried. If the solvent in the wet gel is removed under supercritical conditions, a material commonly called an "aerogel" is obtained. If the gel is dried via freeze drying (lyophilization), the resulting material is commonly referred to as a "cryogel." Drying at ambient temperature and ambient pressure leads to what is commonly referred to as a "xerogel." Other drying possibilities are available including elevated temperature drying (e.g., in an oven), vacuum drying (e.g., at ambient or elevated temperatures), and so forth. Further information concerning sol-gel materials can be found, for example, in Viitala R. et al., "Surface properties of in vitro bioactive and non-bioactive sol-gel derived materials," *Biomaterials*, 2002 August; 23(15):3073-86, incorporated by reference herein.

Composite coatings in accordance with the present invention may be formed based upon analogous processes, as well as upon principles of polymer synthesis and manipulation. Sol gel processes are suitable for use in conjunction with polymers and their precursors, for example, because they can be performed at ambient temperatures. A review of various techniques for generating polymeric-ceramic composites can be found, for example, in G. Kickelbick, "Concepts for the incorporation of inorganic building blocks into organic polymers on a nanoscale," *Prog. Polym. Sci.*, 28 (2003) 83-114, incorporated by reference herein.

Using these and other techniques, coatings can be formed that comprise (a) a polymeric portion comprising a PVP block (e.g., PVP, a block copolymer with one or more PVP blocks and one or more additional PVP blocks, a blend of PVP and another polymer, etc.) and (b) an inorganic portion comprising one or more metal or semi-metal oxides, for example, silicon oxide, germanium oxide, aluminum oxide, zirconium oxide, titanium oxide, iron oxide, hafnium oxide, niobium oxide, tantalum oxide, molybdenum oxide, tungsten oxide, rhenium oxide, iridium oxide, barium oxide, as well as combinations of two or more of the preceding oxides.

Such composite coatings may be formed, for example, by first forming a gel (e.g., a xerogel, cryogel, etc.) on a medical substrate. The gel is then impregnated with one or more monomers. For example, the gel may be impregnated with vinyl pyrrolidone. As another example, the gel may be impregnated with a PVP macro-monomer (e.g., PVP with a terminal unsaturated group such as a vinyl group) and one or more additional monomers (e.g., monomers corresponding to the optional additional polymer blocks described above, for instance, a monomer having a vinyl group). The monomers are then polymerized. As another example, the gel may be impregnated with a PVP-containing polymer (e.g., PVP, a block copolymer with one or more PVP blocks and one or more additional PVP blocks, etc.), or a blend of a PVP-containing polymer and one or more other polymers.

Composite coatings may also be formed, for example, by conducting sol gel processing in the presence of preformed polymers (e.g., PVP, a block copolymer with one or more PVP blocks and one or more additional PVP blocks, a blend of PVP and another polymer, etc.) on a medical substrate. For example, a polymeric coating may first be formed on a medical substrate, followed by the introduction of inorganic precursors (e.g., metal and/or semi-metal alkoxides) to the polymeric coating. As another example, a polymer solution may be combined with a sol (or with a solution of inorganic precursors, e.g., metal and/or semi-metal alkoxides, which form a sol after hydrolysis/condensation occurs) and the combined solution applied to a medical substrate.

As a specific example of how a composite material may be formed, C.-K. Chan et al. *Materials Letters* 58 (2004) 2243-2247, incorporated by reference herein, describe the synthesis of a composite material of inorganic silica and PVP, based on the sol-gel processing of tetraethyloxysilane (TEOS) or methyltriethyloxyslane (MTEOS) in the presence of PVP.

Other techniques result in covalent interactions between the polymeric and inorganic portions of the composite coatings. Examples of such techniques include the following: (a) providing a polymer or polymers that have ceramic precursor groups (e.g., PVP, or a block copolymer with one or more PVP blocks and one or more additional blocks, having groups that are capable of participation in hydrolysis/condensation, for instance, metal or semi-metal alkoxide groups), along with optional additional ceramic precursors (e.g., metal or semi-metal alkoxides), followed by hydrolysis/condensation to form a sol, which may be applied to a medical substrate, (b) providing a ceramic sol with polymer precursor groups (e.g., groups that are capable of participation in a polymerization reactions, such as vinyl groups) and thereafter conducting a polymerization reaction on a medical substrate in the presence of monomers (e.g., vinyl pyrrolidone, or vinyl pyrrolidone and one or more optional additional monomers, or a PVP macromer and one or more optional additional monomers, etc.), and (c) providing species with both polymeric and ceramic precursor groups (e.g., those polymeric and ceramic precursor groups described above, among others) and thereafter conducting hydrolysis/condensation and polymerization on a medical substrate.

Composite coatings may be formed directly on medical substrates (e.g., implantable or insertable medical devices, or components thereof). Alternatively, a composite material may be preformed and subsequently applied to a medical substrate. For example, a composite material may be preformed which has thermoplastic characteristics, in which case it may be heated to form a melt for further processing. Such melts may be applied to a medical substrate to form a composite coating. In other embodiments, for example, extrusion and co-extrusion techniques, the composite coating and the underlying substrate are formed simultaneously.

Other descriptions of composite materials comprising a sol-gel derived inorganic portion and a polymeric portion that comprises a PVP block include, for example, M. Yoshida et al., "Sol-Gel-Processed $SiO_2/TiO_2$/Poly(vinylpyrrolidone) Composite Materials for Optical Waveguides," *Chem. Mater.*, 8 (1), 235-241, 1996; M. Zheng et al., "Preparation, structure and properties of $TiO_2$-PVP hybrid films," *Mater. Sci. Eng., B, Solid-State Mater. Adv. Technol.* 77(1) 2000 55-59; J. Shen et al., "Preparation of zirconia thin films via sol-gel process from inorganic precursor," *Proc. SPIE* Vol. 4086, p. 406-409, 2000, Fourth International Conference on Thin Film Physics and Applications; M-P Zheng et al., "Characterization of $TiO_2$-PVP nanocomposites prepared by the sol-gel method," *Journal of Materials Science Letters*, 19(5) 2000 433-436; and K. Takana et al., "Sol-Gel Preparation and Mechanical Properties of Machinable Cellulose/Silica and Polyvinylpyrrolidone/Silica Composites," *Chemistry and Material Science* 32(1-3) 2004 pp 73-77, each of which is incorporated by reference herein.

Another method by which composite coatings in accordance with the present invention may be formed over suitable substrate materials is chemical vapor deposition. For example, K. Chan et al., *Polymer* 47 (2006) 6941-6947 and Martin et al., "Initiated chemical vapor deposition of antimicrobial polymer coatings," *Biomaterials* 28 (2007) 909-915, each of which are incorporated by reference herein, describe the use of initiated chemical vapor deposition (iCVD) for the deposition of PVP. Initiated chemical vapor deposition can be combined with other methods to create composite PVP-inorganic materials. For example, any suitable method for creating nano-particles can be employed subsequently followed by iCVD. For example, glancing angle deposition (GLAD) can be employed for the generation of inorganic nanostructures followed by iCVD for the deposition of PVP. See also Zhao et al, "Designing Nanostructures by Glancing Angle Deposition," *Proceedings of SPIE* Vol. 5219, 59-73 and US Patent Publication No. 2007/0104860, Initiated Chemical Vapor Deposition of Vinyl Polymers for Encapsulation of Particles, the entire content of which is incorporated by reference herein.

One advantage of sol-gel based techniques and CVD techniques is that they can be used to form composite coatings having interpenetrating polymer and ceramic portions.

Once a composite coating is formed, for instance, by the above or other methods, the ratio of the inorganic portion to the polymeric portion within the composite coating may be further tuned by calcination (in order to remove a portion of the polymeric component) or by selective dissolution of the inorganic polymer brush cores (in order to remove a portion of the inorganic component).

In accordance with some embodiments of the invention, it is desirable to provide an inorganic barrier coating between a polymeric substrate and a PVP-containing composite coating. For example, the inorganic barrier coating may prevent migration of substances from the polymer substrate (e.g., residual non-polymeric species such as residual monomers, residual crosslinking agents, residual initiators, etc.) into the PVP-containing composite coating and vice versa. Suitable materials for inorganic barrier coatings may be selected from those set forth above in connection with substrate materials, among others. The inorganic barrier coating will typically contain at least 10 wt % inorganic material, more typically 50 wt % to 75 wt % to 90 wt % to 95 wt % to 97 wt % to 99 wt % or more inorganic material.

In certain embodiments of the invention, a first composite coating is applied to a polymeric substrate, which first composite coating contains an inorganic portion and a polymeric portion that contains one or more polymer blocks that match one or more polymer blocks in the underlying polymeric substrate (e.g., to provide good adhesion). Then, either stepwise or gradually, the polymer content of the first composite coating is reduced to provide a substantially pure inorganic coating (which has greater barrier properties than the composite material). Finally, either stepwise or gradually, the polymer content is increased such that the outer layer(s) of the coating correspond(s) to a PVP-containing composite coating in accordance with the invention.

As a specific example, PEBAX, a segmented block copolymers with alternating nylon-12 hard blocks and polytetramethylene oxide soft blocks, contains residual laurolactam, which can migrate and crystallize within PVP. In certain embodiments of the present invention, this may be prevented by introducing an inorganic barrier coating between an underlying substrate containing the laurolactam and the overlying PVP-containing composite coating. For example, a first composite coating containing a sol-gel derived inorganic portion selected from silica, titania and/or zirconia and a polyether-block-polyamide, a polyether or a polyamide (for compatibility with the PEBAX) may be initially deposited on the PEBAX. Examples of such coatings are described, for example, in R. A. Zoppi et al., "Hybrids of Poly(ethylene oxide-b-amide-6) and $ZrO_2$ Sol-gel: Preparation, Characterization, and Application in Processes of Membranes Separation," *Advances in Polymer Technology*, 21(1), 2006, 2-16; R. A. Zoppi et al., "Hybrid films of poly(ethylene oxide-b-amide-6) containing sol-gel silicon or titanium oxide as inorganic fillers: effect of morphology and mechanical properties on gas permeability," *Polymer* 41 (2000) 5461-5470; and M. L. Sforca et al., "Hybrid Membranes Based on $SiO_2$/Polyether-b-Polyamide: Morphology and Applications," *Journal of Applied Polymer Science*, 82(1), 2001, 178-185, each of which is incorporated by reference herein. Then, a pure ceramic coating may be applied over the first composite coating, for example, a sol-gel-derived or vapor-deposited coating of silica, titania and/or zirconia (for barrier properties). Finally, a composite coating that contains an inorganic portion and a PVP-containing polymeric portion in accordance with the invention is deposited (e.g., by sol-gel processing, CVD, etc.) (for wear resistance, biocompatibility, etc.).

As noted above, in certain embodiments, one or more therapeutic agents are provided within and/or beneath the composite coatings of the present invention. "Therapeutic agents," "biologically active agents," "drugs," "pharmaceutically active agents," "pharmaceutically active materials," and other related terms may be used interchangeably herein and include genetic therapeutic agents, non-genetic therapeutic agents and cells.

A wide variety of therapeutic agents can be employed in conjunction with the present invention. Only a few examples of therapeutic agents are described here. These include anti-restenotic agents, anti-proliferative agents, anti-thrombotic agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms, and combinations of two or more of the foregoing, among others.

Specific examples of therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), and combinations of two or more of the foregoing, among others.

Various techniques may be employed in incorporating the therapeutic agent(s) into the composite coatings of the present invention.

For instance, therapeutic agent(s) may be incorporated by contacting them with previously formed composite coatings. For instance, a fluid containing dissolved or dispersed therapeutic agent may be contacted with composite coating by dipping, spraying, coating with an applicator (e.g., by roller or brush), spin-coating, web coating, techniques involving coating via mechanical suspension including air suspension, ink jet techniques, and combinations of these processes, among other techniques. Water, organic solvents, subcritical fluids, critical point fluids, supercritical fluids, and so forth can be used as carriers for the therapeutic agent.

In other instances, therapeutic agent(s) may be incorporated during the formation of the composite coating. For example, where the composite coating is formed from a single formulation (e.g., a solution, suspension, melt, etc.) containing all of the molecular elements required for the formation of the composite coating, the therapeutic agent(s) may be added to that formulation, among numerous other possibilities.

Although various embodiments are specifically illustrated and described herein, it will be appreciated that modifications and variations of the present invention are covered by the above teachings and are within the purview of the appended claims without departing from the spirit and intended scope of the invention. For example, as will be appreciated by those of ordinary skill in the art, composite coatings may be formed using various methods other than those set forth above, including electrostatic layer-by-layer self assembly, colloidal deposition, vacuum deposition and cathodic electrophoretic deposition techniques, among others.

The invention claimed is:

1. A medical device comprising (a) a polymeric substrate that comprises a first polymer block, (b) an inorganic barrier coating over the polymeric substrate, and (c) a first composite coating over the inorganic barrier coating, said first composite coating comprising (i) a first inorganic portion and (ii) a first polymeric portion that comprises a poly(vinyl pyrrolidone) block, wherein said medical device is an implantable or insertable medical device, wherein the first inorganic portion comprises an inorganic oxide selected from oxides of silicon, germanium, titanium, zirconium, aluminum, tantalum, iridium, ruthenium, barium and combinations thereof.

2. The medical device of claim 1, wherein said medical device is a balloon.

3. The medical device of claim 1, wherein the first inorganic portion comprises a sol-gel-derived inorganic oxide or a vapor deposited inorganic oxide.

4. The medical device of claim 1, wherein the first inorganic portion comprises inorganic nanoparticles.

5. The medical device of claim 1, wherein the barrier coating is a sol-gel derived barrier coating or a vapor deposited barrier coating.

6. The medical device of claim 1, further comprising an additional composite coating between the polymeric substrate and the inorganic barrier coating, wherein the additional composite coating comprises (i) a second inorganic portion which may be the same as or different from the first inorganic portion and (ii) a second polymeric portion that comprises a polymer block having the same monomer composition as said first polymer block.

7. The medical device of claim 6, wherein the substrate comprises polyether and polyamide blocks, and wherein the second polymeric portion comprises a polyamide block, a polyether block, or both.

8. The medical device of claim 1, further comprising a therapeutic agent disposed beneath the first composite coating, within the first composite coating, or both.

9. The medical device of claim 8, wherein the therapeutic agent is selected from anti-restenotic agents, anti-proliferative agents, anti-thrombotic agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms, and combinations of two or more of the foregoing.

10. A medical device comprising (a) a polymeric substrate that comprises a first polymer block, (b) an inorganic barrier coating over the polymeric substrate, and (c) a first composite coating over the inorganic barrier coating, said first composite coating comprising (i) a first inorganic portion and (ii) a first polymeric portion that comprises a poly(vinyl pyrrolidone) block, wherein the first inorganic portion comprises inorganic nanoparticles selected from carbon nanoparticles, metallic nanoparticles, metal oxide nanoparticles, silicon oxide nanoparticles, silicate nanoparticles, polyhedral oligomeric silsequioxanes, polyoxometalate nanoparticles, and combinations thereof.

* * * * *